United States Patent
Dodds

(10) Patent No.: US 11,406,681 B2
(45) Date of Patent: *Aug. 9, 2022

(54) COMPOUND FOR TREATING OXIDATIVE STRESS IN MAMMALS

(71) Applicant: Hemopet, Garden Grove, CA (US)

(72) Inventor: Winifred Jean Dodds, Santa Monica, CA (US)

(73) Assignee: HEMOPET, Garden Grove, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/501,309

(22) Filed: Oct. 14, 2021

(65) Prior Publication Data

US 2022/0031795 A1 Feb. 3, 2022

Related U.S. Application Data

(63) Continuation-in-part of application No. 17/114,217, filed on Dec. 7, 2020.

(60) Provisional application No. 62/953,049, filed on Dec. 23, 2019.

(51) Int. Cl.

| | |
|---|---|
| A61K 36/9068 | (2006.01) |
| A61K 31/593 | (2006.01) |
| A61K 33/04 | (2006.01) |
| A61K 31/385 | (2006.01) |
| A61K 9/00 | (2006.01) |
| A61K 36/82 | (2006.01) |
| A61K 36/9066 | (2006.01) |
| A61K 36/88 | (2006.01) |
| A61K 36/484 | (2006.01) |
| A61K 31/122 | (2006.01) |

(52) U.S. Cl.
CPC ........ *A61K 36/9068* (2013.01); *A61K 9/0056* (2013.01); *A61K 31/122* (2013.01); *A61K 31/385* (2013.01); *A61K 31/593* (2013.01); *A61K 33/04* (2013.01); *A61K 36/484* (2013.01); *A61K 36/82* (2013.01); *A61K 36/88* (2013.01); *A61K 36/9066* (2013.01)

(58) Field of Classification Search
None
See application file for complete search history.

(56) References Cited

U.S. PATENT DOCUMENTS

| | | |
|---|---|---|
| 6,455,083 B1 | 9/2002 | Wang |
| 7,833,795 B2 | 11/2010 | Fitzgerald |
| 9,585,925 B1 | 3/2017 | Bascharon |
| 10,989,717 B1 | 4/2021 | Dodds et al. |
| 2003/0119064 A1 | 6/2003 | Valkirs et al. |
| 2005/0100979 A1 | 5/2005 | Power |
| 2005/0249788 A1 | 11/2005 | Reynolds et al. |
| 2011/0287109 A1* | 11/2011 | Bagley ............. A61K 31/355 424/638 |
| 2016/0202272 A1 | 7/2016 | Dahl et al. |

FOREIGN PATENT DOCUMENTS

WO 2005059566 A1 6/2005

OTHER PUBLICATIONS

Torzewski, et al., "Animal Models of C-Reactive Protein," Hindawl Publishing Corporation, Mediators of Inflammation, vol. 2014, pp. 1-7, 2014.

Van Der Vekiens, et al., "Human and equine cardiovascular endocrinology: beware to compare," Cardiovascular Endocrinology, vol. 2, No. 4, pp. 67-76, 2013.

Iacopetti, I., et al., "Salivery pH, calcium, phosphorus and selected enzymes in healthy dogs: a pilot study," BMC Veterinary Research, pp. 1-17 (2017).

Milne, G. L., "Classifying oxidative stress by F2 Isoprostane levels in human disease: The re-imagining of a biomarker" Redox Biology 12:897-898 (2017).

* cited by examiner

*Primary Examiner* — Terry A McKelvey
*Assistant Examiner* — Catheryne Chen
(74) *Attorney, Agent, or Firm* — Greenberg Traurig, LLP

(57) ABSTRACT

Managing and treating elevated OS biomarkers in mammals such as companion animals with at least one of the supplements alpha-lipoic acid, carnitine, co-enzyme Q-10, ginger, green tea, licorice, milk thistle, garlic, honey. resveratrol, soybeans, tomatoes, turmeric, vitamin D, vitamin E or selenium. Diagnosing an oxidative stress (OS) in a mammal comprises collecting a sample; screening the sample to detect the presence of an OS biomarker, selectively isoprostane and other antioxidants such as HODE microRNAs. TAC: GSH, MDA, and TNF-alpha. The sample can be saliva.

22 Claims, No Drawings

COMPOUND FOR TREATING OXIDATIVE STRESS IN MAMMALS

CROSS REFERENCE TO RELATED APPLICATIONS

This application is a continuation in part of U.S. patent application Ser. No. 17/114,217, filed on Dec. 7, 2020, entitled COMPOUND FOR TREATING OXIDATIVE STRESS IN ANIMALS, which claims benefit of priority of US Provisional Patent App. No. 62/953,049, filed Dec. 23, 2019, entitled OXIDATIVE STRESS BIOMARKERS TESTING IN ANIMALS, the contents of each of which is incorporated by reference in its entirety herein.

This application also relates to U.S. Pat. No. 10,989,717, entitled OXIDATIVE STRESS BIOMARKERS TESTING IN ANIMALS by W. Jean Dodds and Denis M. Callewaert and allowed U.S. patent application Ser. No. 17/207,254, filed Mar. 19, 2021, entitled OXIDATIVE STRESS BIOMARKERS TESTING IN CANINES by W. Jean Dodds and Denis M. Callewaert. The contents of those applications and the patent are incorporated by reference in its entirety herein.

BACKGROUND

The present disclosure is directed to cellular oxidative stress treatment in mammals such as companion animals.

In people and animals, cells in homeostatic equilibrium are in a state of oxidative balance, namely, when there are sufficient cellular antioxidants (both small molecule radical scavengers and enzymes such as catalase and superoxide dismutase) to avoid a buildup of excess free radicals (oxidizing agents). However, when levels of oxidizing agents exceed antioxidants, the condition is termed oxidative stress (OS). OS is now known to trigger inflammatory responses and to be an underlying cause of most chronic diseases.

Extensive investigations of OS and chronic tissue inflammatory responses have established that they are major underlying risk factors that play key roles in the etiology of a range of human (and animal) diseases, including rheumatoid arthritis, cancers, diabetes, obesity, periodontal disease, neurodegenerative disorders, and cardiovascular diseases. The development and progression of these chronic diseases is influenced by a range of environmental, dietary, and lifestyle factors, and specific dietary components, that— along with exercise and some nutraceuticals'can significantly impact OS and inflammation.

Chronic inflammation resulting from increased free radical formation in OS, also called reactive oxygen species (ROS), occurs when tissues or organs receive inflammatory "mediator" messages that cause them to react as though a "trigger" such as a pathogen is present. Rather than repairing themselves, these cells can remain in an ongoing state of inflammation that can wax and wane for prolonged periods. Tissues thus become deficient in antioxidant mediators, such as glutathione, cysteine, ascorbic acid and other radical scavenging vitamins, as well as superoxide dismutase, catalase and other antioxidant enzymes, and these deficiencies are strongly correlated with poor clinical outcomes. For mammals in good health, ~25% of oxygen intake gives rise to ROS, whereas this increases with age and poor health to as much as 75%.

When cells undergo damage due to OS and inflammation, the incidence and severity of infections, obesity cardiovascular disease and cancers increase. These damaged cells release molecules that can be used as biomarkers for OS and inflammation. Biomarkers of clinical relevance in people and pets include isoprostanes, malondialdehyde, and several cytokines including tumor necrosis factor (TNF), hydroxyoctadecadienoic acid (NODE), as well as certain microRNAs. Elevated levels of these biomarkers in biofluids (including plasma, urine and/or saliva) can be used to evaluate oxidative status and can addressed with diet and supplement changes to promote beneficial antioxidant effects. On the other hand, alternative biomarkers, such as glutathione, certain microRNAs, and some enzymes are indicative of a healthy antioxidant condition. Biomarkers can be analyzed assays periodically to assess the response and adjust lifestyle, nutritional and nutraceutical therapy, as needed.

Significant efforts have been made toward the dietary management of OS. In contrast to small molecule antioxidants (e.g., ascorbic acid) that can neutralize one ROS/molecule, recent studies have focused on the development of functional foods, e.g., those containing natural Nrf-2 activators since Nrf-2 upregulates expression of multiple antioxidant enzymes including superoxide dismutase, catalase, glutathione transferases and glutathione reductase. A single molecule of one of these enzymes can neutralize a huge number of ROS. Significant amounts of antioxidant radical scavengers and/or Hrf-2 activators are ingredients in many functional foods and supplements such as: turmeric (*Curcuma longa*); and its relative, ginger (*Zingiber officiale*); chili peppers (*Capsicum annuum*); green tea (*Camellia sinensis*, which contains tannins and polyphenol catechins, and other teas); soybeans (*Glycine max*); tomatoes (*Solanum lycopersicum*, rich in lycopenes); grapes (not for pets); honey (not for infants or very young animals); cranberries (*Vaccinium macrocarpon*, contains pro-anthocyanidins); licorice (*Glycyrrhiza glabra*); garlic (*Allium sativum*, in moderation for pets); milk thistle (*Silybum marianum*); cabbages and broccoli.

Some Primary Oxidative Stress Biomarkers

Isoprostanes are a series of prostaglandin-like compounds produced by non-enzymatic ROS-catalyzed peroxidation of arachidonic acid. The concentration of isoprostanes is considered the "gold standard" for quantifying OS in vivo in humans and certain animals.

MicroRNAs are small non-coding RNA molecules found mostly in the cells of plants, animals and some viruses. They function in RNA silencing and post-transcriptional regulation of gene expression. The function of microRNAs is in gene regulation.

Reduced glutathione (GSH) plays two key roles in the maintenance of redox balance. First, GSH is a major intracellular radical scavenger that can react with and neutralize ROS thus preventing ROS-mediated damage to macromolecules such as proteins and DNA.

GSH is also a co-substrate for Glutathione-S-Transferases (GSTs), a superfamily of isozymes best known for their ability to catalyze the conjugation of the reduced form of glutathione (GSH) to foreign substrates for the purpose of detoxification. https://en.wikipedia.org/wiki/Glutathione S-transferase—cite note-pmid15717864-1 are found in plants, animals, fungi, and some bacteria. In vertebrates there are over 18 distinct cytosolic GSTs which are expressed most tissues, but especially in liver, kidney, heart, lung, and brain tissues. High levels of GST are associated with resistance to the apoptosis (cell death) induced by a range of substances, including chemotherapeutic agents. The levels of specific GST isoforms in urine and serum are indicators of hepatocyte and renal tubular injury in transplantation, toxicity and viral infections of humans and rodents.

The production of GSH is dependent on the enzyme glutathione reductase (GSR), and the expression of GSR, as well as multiple cytosolic GSTs and other antioxidant enzymes including superoxide dismutase are upregulated by the transcription factor Nrf-2. Therefore, while direct measurement of Nrf-2 activation by diet, nutraceuticals, etc. is extremely difficult, the levels of glutathione in biological fluids can serve as a surrogate biomarker for Nrf-2 activation.

Malondialdehyde (MDA) is a key byproduct of the peroxidation of polyunsaturated fatty acids. It is very reactive and forms adducts with macromolecules, thereby altering or eliminating their function. MDA and/or MDA adducts are well established biomarkers for OS. However, some methods for the measurement of MDA, including the thiobarbituric acid reactive substance (TBARS) assay as it was traditionally performed do not provide consistent reliable results. Malondialdehyde is potentially mutagenic, and has been found in heated edible oils such as sunflower and palm oils. Corneas of human patients suffering from keratoconus and bullous keratopathy have increased levels of malondialdehyde, and this aldehyde also can be found in tissue sections of joints from human patients with osteoarthritis.

Tumor Necrosis Factor-Alpha (TNF-α), also called cachexin or cachectin, is a cell signaling protein involved in systemic inflammation and is one of the cytokines that play a primary role in the acute phase inflammatory response. It is produced chiefly by activated macrophages, although it can be produced by many other cell types such as CD4+ lymphocytes, natural killer (NK) cells, neutrophils, mast cells, eosinophils, and even neurons. https://en.wikipedia.org/wiki/Tumor necrosis factor alpha—cite note-ReferenceA-5

TNF is an endogenous pyrogen that can induce fever, apoptotic cell death, cachexia, inflammation, inhibit tumorigenesis and viral replication, and respond to sepsis via interleukin IL-1 and IL-6 producing cells. Dysregulation of TNF production has been implicated in a variety of human diseases such as Alzheimer's disease, cancer, depression, psoriasis and inflammatory bowel disease (IBD).

Hydroxyoctadecadienoic Acid (HODE) is a lipid peroxidase biomarker found to be elevated for early detection of periodontal disease, type-2 diabetes, rheumatoid arthritis, cataracts, Alzheimer's disease and hepatitis-B and -C in people.

Other Biomarker Enzymes include: Sorbitol Dehydrogenase, a cytosolic enzyme that converts sorbitol, the sugar alcohol form of glucose, into fructose; and 5' Nucleotidase, which catalyzes the phosphorolytic cleavage of 5' nucleotides, and is considered a maturation marker for T- and B-cells.

Measuring Biomarkers of Oxidative Stress

Traditionally, cellular biomarkers are measured in the serum and/or urine from humans and animals. However, collecting these samples especially from children and smaller animal species presents with difficulty and causes unnecessary stress.

Neither canine whole blood-, serum-, nor urine-based isoprostane quantitations are accurate, linear and predictive as a marker for tissue oxidative stress in the canine species. Similarly, there are no published studies of measuring HODE as a biomarker of OS in companion animals There is a need for another form of OS testing in companion animals, especially canines.

Managing and Treating Elevated Biomarkers of Oxidative Stress. Use of treatments and preventive health measures including applicable drugs, diets, supplements and exercise.

SUMMARY

The disclosure includes management and treatment measures to alleviate elevated oxidative stress biomarkers and their clinical expression in companion animals such as dogs or cats, and other animal species.

According to the disclosure, measurement is affected in bodily fluids, selectively saliva.

Collection of saliva is noninvasive, painless, relatively inexpensive and convenient for the individual. Salivary testing of OS and/or inflammatory biomarkers can reveal the latent or pre-clinical form of developing OS.

There is a need to provide for practical and rapid screening or testing for OS to permit enhancement of the health of animals. Current methods and findings in humans and rodents measure OS biomarkers primarily in serum or urine. However, while one can measure OS biomarkers in healthy dog serum, neither serum nor urine has provided reliable quantitative and linear measurements in healthy dogs or especially in those with chronic diseases, where one would predict their elevation from tissue OS.

In accordance with this disclosure there is provided a diagnostic test system for OS stress assessment in animals, in particular companion animals, such as dogs, cats, rabbits, hamsters, and horses.

Saliva can be used as a diagnostic tool to assess the health or disease status of an animal. Saliva is easily collected, stored and shipped, and provides a non-invasive means of multiple or serial sampling for use as a diagnostic tool for a variety of conditions in animals.

The disclosure uses a species-specific test for companion animals such as dogs or cats, and other animal species, and the appropriate methods.

The disclosure is further described in detail.

DETAILED DESCRIPTION

Different biomarkers are described and different abbreviations below are as follows.

IsoP, isoprostane(s); AOX, antioxidant capacity; CRP, C-reactive protein; GSH, glutathione; MDA, malonaldehyde; NO, nitric oxide; TAC, total antioxidant capacity; transcription factor Nrf-2 (Nuclear factor erythroid 2-related factor 2), TNF-alpha, tumor necrosis factor-alpha, and HODE, hydroxyoctadecadienoic acid.

The disclosure provides a straightforward, reliable assay for OS biomarkers and for antioxidant capacity of biological fluids.

The present disclosure relates to a test for levels of oxidized lipid biomarkers, selectively isoprostanes, HODE, microRNA and other biomarkers for animals, particularly companion animals and more particularly dogs, cats or horses using saliva that permits the rapid, accurate, non-invasive quantitative screening for biolipids, selectively in the animal.

The saliva-based test assay quantifies the isoprostane, HODE and microDNA levels in dog saliva to determine if the pet's body is undergoing harmful OS. OS creates reactive oxygen species (ROS) causing cells to undergo damage and release biomarker lipids and enzymes that lead to tissue inflammation, infections, periodontal disease, obesity and even cancers. However, free radicals themselves are so reactive and short-lived that direct measurement is not possible. Thus, isoprostane and HODE levels serve as reliable surrogate biomarkers for the presence of ROS.

The saliva-based tests of this disclosure are novel isoprostane, HODE and microRNA tests, and are examples of a set of unique biomarker tests for pets that can be measured in saliva.

For quantitative testing, an animal's serum or saliva or other bodily fluid is added to the ELISA microtiter plate or other immunoassay platforms such as but not limited to lateral flow, or latex or bead agglutination, which measures the presence of cellular oxidative stress.

Once collected at or received by the lab, the blood serum or saliva or other bodily fluid sample is then screened using the ELISA method or other immunoassay platforms such as but not limited to lateral flow, or latex or bead agglutination, which measures the presence of OS.

Forms of biological fluid, other than saliva, for instance urine, tears, sweat, or milk or other mucosal secretions can be used.

The detection of cellular oxidative stress can be performed with an immunoassay. Immunoassays include, but are not limited to, ELISA test, RIA test, latex agglutination, beads assay, and proteomic assays. A preferable immunoassay is the ELISA test. Other immunoassays can be used and the choice of immunoassay can be determined by one of ordinary skill in the art.

A method for diagnosing OS in a mammal such as a human, dog or other companion animal comprises the steps of collecting a sample of saliva; screening the sample to detect a level of at least one of a number of OS markers and detecting and diagnosing the presence of OS based on the level of one or more markers.

A method for diagnosing OS in a mammal such as human, dog or other companion animal comprises the steps of collecting a sample of saliva; screening the sample to detect a level of at least one isoprostane, and detecting and diagnosing the presence of OS based on the quantitative level of the isoprostane.

A method for diagnosing OS in a mammal such as human, dog or other companion animal comprises the steps of collecting a sample of saliva; screening the sample to detect a level of at least one HODE, and detecting and diagnosing the presence of OS based on the quantitative level of the HODE.

The method further comprises collecting a first testing portion of the saliva sample and wherein the first testing portion is the sample for use in the screening step. [Glucuronidase pretreatment is not required for saliva samples.]

The method includes the screening step utilizes an enzyme-linked immunosorbent assay (ELISA) testing system to detect the level of the saliva-based OS marker.

Results

After completing the initial clinical trial studies, analyzing 282 clinical patient samples; 79 of them (35%) were positive, having isoprostane biolipid levels, for example, above the normal reference range we have established (i.e., 0.5-1.75 ng/mL of saliva).

Of the 79 positive testing dogs, there were: 34% spayed females, 32% neutered males, 21% intact males and 15% intact females. The ages ranged from 4 months to 15 years, although most were middle aged or older. The weight range was 4-143 pounds, with 84% being medium to large or giant in size; no breed type predominated.

The diets fed the 79 positive dogs included: 40% ate only a commercial raw diet; 20% only a commercial dry kibble; 13% a home cooked or home prepared raw diet, and 3% ate a combination of a commercial kibble and raw.

Of the 79 positive dogs, 38 also had saliva-based profiles run for food sensitivity and intolerances to 24 foods. Interestingly, only 3 of these 38 dogs had Saliva based test results that were reactive (20 or more foods). These results suggest that dogs with clinical issues related to intense itching, scratching, chewing, and bowel irritability had relatively few identified foods as the culprits. Environmental exposure to inhalants, fleas, ticks, mites and other insects as well as contact reactants could be involved; and 3 dogs were taking an isooxazoline parasiticide.

Positive testing dogs should be retested in about 6 months after being on foods and supplements designed to lower their OS. The beneficial outcome of 50 isoprostane positive samples revealed reduced isoprostane levels when retested 5-6 months after taking the supplements listed below.

Management and Treatment

Management and treatments measures to alleviate elevated oxidative stress biomarkers of at least isoprostane and/or HODE, and their clinical expression in companion animals such as dogs or cats, and other animal species are described below. Use of supplements for isoprostane and HODE can be used for any other biomarkers of OS such as MicroRNAs PGF2a, MDA, TAC and others. Supplements that are used to bring down high levels of isoprostane and/or HODE are:

Alpha-Lipoic acid in an amount between 50 mg and 100 mg Carnitine
Co-Enzyme Q-10 in an amount between 5 mg and 20 mg Ginger
Green tea in an amount between 50 mg and 200 mg Licorice
Milk thistle, and a few more like garlic and honey.
Resveratrol (as a natural supplement or as food like blueberries and cranberries)
Selenium in an amount between 5 mcg and 20 mcg Soybeans
Tomatoes
Turmeric (curcumin)—without black pepper for pets in an amount between 20 mg and 300 mg
Vitamin D in an amount between 25 mcg and 150 mcg
Vitamin E Supplements that are used to bring down high levels of isoprostane and/or HODE are:

Alpha-Lipoic acid in an amount between 50 mg and 100 mg
Co-Enzyme Q-10 in an amount between 5 mg and 20 mg
Green tea in an amount between 50 mg and 200 mg
Selenium in an amount between 5 mcg and 20 mcg
Turmeric (curcumin) in an amount between 20 mg and 300 mg
Vitamin D in an amount between 25 mcg and 150 mcg One Supplement formulation used to bring down high levels of isoprostane and/or HODE are:

Alpha-Lipoic acid in an amount of about 20 mg
Co-Enzyme Q-10 in an amount of about 10 mg
Green tea in an amount of about 100 mg
Selenium in an amount of about 10 mcg
Turmeric (curcumin) in an amount of about 100 mg
Vitamin D in an amount of about 75 mcg A synergistic biological effect of mutual benefit, based upon the principle of cooperative symbiosis, is achieved by this group of ingredients.

Two or more of Alpha-Lipoic acid; Carnitine, Co-Enzyme Q-10, Ginger, Green tea, Licorice, and Milk thistle produce enhanced and thus are synergistic.

The synergy results from the interaction between nutrients, their absorption and bioavailability in the body which in this situation is positive and provides health benefits. Evidence-based studies have illustrated that the active components in the nutritional supplements of the disclosed supplements work together synergistically to enhance their functional properties in preventing diseases and betterment of health. The role of the disclosed nutritional supplements working together enhances treatment and prevention of chronic diseases, such as cardiovascular and periodontal disease, infections, dysbiosis, diabetes, obesity, and cancers. This combination synergic effect is a scientific advance in nutritional therapy and significantly brings down high levels of isoprostane and/or HODE more effectively than when the supplements are separately used.

Additional synergistic effects can be obtained with Garlic and honey, Resveratrol (as a natural supplement or as food like blueberries and cranberries); Selenium; Soybeans; Tomatoes; Turmeric (curcumin); Vitamin D; and Vitamin E.

Each of these individually produce overtly similar effects, they display greatly enhanced effects when given in combination. The combined effect is greater than that predicted by their individual potencies, and thus the combination is synergistic.

The compound of the disclosure includes treating an elevated isoprostane OS biomarker with at least one of alpha-lipoic acid, co-enzyme Q-10, green tea, turmeric, vitamin D, or selenium.

The method of the disclosure includes treating an elevated isoprostane OS biomarker and an elevated HODE OS biomarker with at least one of alpha-lipoic acid, co-enzyme Q-10, green tea, turmeric, vitamin D, or selenium.

The compound of the disclosure includes treating an elevated HODE OS biomarker with at least one of alpha-lipoic acid, co-enzyme Q-10, green tea, turmeric, vitamin D, or selenium.

The compound of the disclosure includes treating an elevated OS biomarker being at least TAC, GSH, MDA, TNF-alpha, NO, and microRNA with at least one of alpha-lipoic acid, co-enzyme Q-10, green tea, turmeric, vitamin D, or selenium.

The compound of the disclosure includes treating an elevated isoprostane OS biomarker with at least alpha-lipoic acid, co-enzyme Q-10, green tea, milk thistle, garlic, honey. resveratrol, soybeans, tomatoes, turmeric, vitamin D, or selenium.

The compound of the disclosure includes treating an elevated HODE OS biomarker with at least alpha-lipoic acid, co-enzyme Q-10, green tea, milk thistle, garlic, honey. resveratrol, soybeans, tomatoes, turmeric, vitamin D, or selenium.

The compound of the disclosure includes treating an elevated isoprostane OS biomarker with at least one of, or with at least two of, or with at least three of, or with at least four of, or with at least five of, or with at least six of, or with at least seven of, or with at least eight of, or with at least nine of, or with at least ten of alpha-lipoic acid, carnitine, co-enzyme Q-10, ginger, green tea, licorice, milk thistle, garlic, honey. resveratrol, soybeans, tomatoes, turmeric, vitamin D, vitamin E or selenium.

The compound of the disclosure includes treating an elevated isoprostane OS biomarker and an elevated HODE OS biomarker with at least one of, or with at least two of, or with at least three of, or with at least four of, or with at least five of, or with at least six of, or with at least seven of, or with at least eight of, or with at least nine of, or with at least ten of: alpha-lipoic acid, carnitine, co-enzyme Q-10, ginger, green tea, licorice, milk thistle, garlic, honey. resveratrol, soybeans, tomatoes, turmeric, vitamin D, vitamin E or selenium.

The compound of the disclosure includes treating an elevated HODE OS biomarker with at least one of, or with at least two of, or with at least three of, or with at least four of, or with at least five of, or with at least six of, or with at least seven of, or with at least eight of, or with at least nine of, or with at least ten of alpha-lipoic acid, carnitine, co-enzyme Q-10, ginger, green tea, licorice, milk thistle, garlic, honey. resveratrol, soybeans, tomatoes, turmeric, vitamin D, vitamin E or selenium.

The compound of the disclosure includes treating an elevated OS biomarker being at least TAC, GSH, MDA, TNF-alpha, NO, and microRNA with at least one of, or with at least two of, or with at least three of, or with at least four of, or with at least five of, or with at least six of, or with at least seven of, or with at least eight of, or with at least nine of, or with at least ten of alpha-lipoic acid, carnitine, co-enzyme Q-10, ginger, green tea, licorice, milk thistle, garlic, honey. resveratrol, soybeans, tomatoes, turmeric, vitamin D, vitamin E or selenium.

The compound of the disclosure includes treating an elevated OS biomarker being at least TAC, GSH, MDA, TNF-alpha, NO, and microRNA with at least one of, or with at least two of, or with at least three of, or with at least four of, or with at least five of, or with at least six of, or with at least seven of, or with at least eight of, or with at least nine of, or with at least ten of: alpha-lipoic acid, carnitine, co-enzyme Q-10, ginger, green tea, licorice, milk thistle, garlic, honey. resveratrol, soybeans, tomatoes, turmeric, vitamin D, vitamin E or selenium.

The proportional decrease in the biomarker level of the oxidative stress, being the value of the isoprostane and/or HODE has been at least 40% and in some cases as much as 90% after about 5-6 months of ingestion of the compounds of the disclosure.

The compound is formulated with the ingredients being mixed together in powdered form and being for ingestion and digestion by the mammal, selectively an animal at least once or twice per day together with the food that is being eaten. In this format, the powder is mixed into the food prior to the food being given to the mammal such as human or animal.

General

Many different formats are possible. In the specification, there have been disclosed typical embodiments of the disclosure. Although specific terms are employed, they are used in a generic and descriptive sense only and not for purposes of limitation, the scope of the disclosure being set out in the claims. It is therefore to be understood that within the scope of the appended claims the disclosure may be practiced otherwise than as described.

The invention claimed is:
1. A method of treating a dog with a diagnosed level above 1.75 ng/ml of the OS isoprostane biomarker comprising:

a. formulating a composition to be a combination of at least vitamin D and selenium, alpha-lipoic acid, co-enzyme Q-10, green tea, and turmeric ingredients,
b. mixing the ingredients together to be for ingestion by the dog,
c. treating the dog with a diagnosed level above 1.75 ng/ml of the OS isoprostane biomarker with the combination composition, and
d. reducing the level below 1.75 ng/ml of the OS isoprostane biomarker in the dog so treated by the composition combination.

2. The method for treating oxidative stress (OS) as claimed in claim 1 including treating an elevated HODE OS biomarker in the dog.

3. The method of claim 1 including reducing the OS isoprostane biomarker level by at least 40%.

4. The method of claim 1 including reducing the OS isoprostane biomarker level by at least 40% after five to six months from an elevated level to a level below 1.75 ng/ml, and measuring the OS isoprostane level in saliva from the dog.

5. A method of treating a dog with a diagnosed level above 1.75 ng/ml of the OS isoprostane biomarker comprising:
   a. formulating a composition as a combination of at least Alpha-Lipoic acid in an amount between 50 mg and 100 mg; Co-Enzyme Q-10 in an amount between 5 mg and 20 mg; Green tea in an amount between 50 mg and 200 mg; Selenium in an amount between 5 mcg and 20 mcg; Turmeric (curcumin) in an amount between 20 mg and 300 mg; Vitamin D in an amount between 25 mcg and 150 mcg; and
   b. treating the dog with a diagnosed level above 1.75 ng/ml of the OS isoprostane biomarker with the combination composition to lower the level below 1.75 ng/ml wherein the OS isoprostane biomarker in the dog so treated by the composition combination is reduced.

6. The method for treating oxidative stress (OS) as claimed in claim 5 including treating an elevated HODE OS biomarker in the dog.

7. The method for treating oxidative stress (OS) as claimed in claim 5 including in the combination cranberries.

8. The method of claim 5 including reducing the isoprostane biomarker level by at least 40%.

9. The method of claim 5 including reducing the isoprostane biomarker level by at least 40% after five to six months from an elevated level to a level below 1.75 ng/ml, and measuring the isoprostane level in saliva from the dog.

10. A method of treating a dog with a diagnosed level above 1.75 ng/ml of the OS isoprostane biomarker comprising:
    a. formulating the composition as a combination at least Alpha-Lipoic acid in an amount of about 20 mg; Co-Enzyme Q-10 in an amount of about 10 mg; Green tea in an amount of about 100 mg; Selenium in an amount of about 10 mcg; Turmeric (curcumin) in an amount of about 100 mg; Vitamin D in an amount of about 75 mcg; and
    b. treating the dog with a diagnosed level above 1.75 ng/ml of the OS isoprostane biomarker with the combination composition to lower the level below 1.75 ng/ml wherein the OS isoprostane biomarker in the dog so treated by the composition combination is reduced.

11. The method for treating oxidative stress (OS) as claimed in claim 10 including treating an elevated HODE OS biomarker in the dog.

12. The method for treating oxidative stress (OS) as claimed in claim 10 including in the combination blueberries.

13. The method of claim 10 including reducing the isoprostane biomarker level by at least 40%.

14. The method of claim 10 including reducing the isoprostane biomarker level by at least 40% after five to six months from an elevated level to a level below 1.75 ng/ml and measuring the isoprostane level in saliva from the dog.

15. A method of treating a dog with a diagnosed level above 1.75 ng/ml of the OS isoprostane biomarker comprising:
    a. using a composition to reduce the isoprostane marker indicative of oxidative stress (OS) in a dog,
    b. formulating the composition as a combination consisting of vitamin D and selenium, alpha-lipoic acid, co-enzyme Q-10, green tea, and turmeric ingredients, and
    c. treating the dog with a level above 1.75 ng/ml of the OS isoprostane biomarker with the combination composition to lower the level below 1.75 ng/ml wherein the OS isoprostane biomarker in the dog so treated by the composition combination is reduced.

16. The method of claim 15 including reducing the isoprostane biomarker level by at least 40%.

17. The method of claim 15 including reducing the isoprostane biomarker level by at least 40% after five to six months from an elevated level to a level below 1.75 ng/ml as measured in saliva from the dog.

18. A method of treating a dog with a diagnosed level above 1.75 ng/ml of the OS isoprostane biomarker comprising:
    a. formulating a composition to consist of a combination of at least Alpha-Lipoic acid in an amount between 50 mg and 100 mg; Co-Enzyme Q-10 in an amount between 5 mg and 20 mg; Green tea in an amount between 50 mg and 200 mg; Selenium in an amount between 5 mcg and 20 mcg; Turmeric (curcumin) in an amount between 20 mg and 300 mg; and Vitamin D in an amount between 25 mcg and 150 mcg;
    b. mixing the ingredients together for ingestion by the dog, and
    c. treating the dog with a diagnosed level above 1.75 ng/ml of the OS isoprostane biomarker with the combination composition to lower the level below 1.75 ng/ml wherein the OS isoprostane biomarker in the dog so treated by the composition combination is reduced.

19. A method of treating a dog with a diagnosed level above 1.75 ng/ml of the OS isoprostane biomarker
    a. using a composition to reduce an isoprostane marker indicative of oxidative stress (OS) in a dog, the composition being a combination consisting of Alpha-Lipoic acid in an amount of about 20 mg; Co-Enzyme Q-10 in an amount of about 10 mg; Green tea in an amount of about 100 mg; Selenium in an amount of about 10 mcg; Turmeric (curcumin) in an amount of about 100 mg; and Vitamin D in an amount of about 75 mcg;
    b. mixing the ingredients together and being for ingestion by the dog, and
    c. treating the dog with a diagnosed level above 1.75 ng/ml of the OS isoprostane biomarker with the combination composition to lower the level below 1.75 ng/ml wherein the OS isoprostane biomarker in the dog so treated by the composition combination is reduced.

20. The method for treating oxidative stress (OS) as claimed in claim 1 including in the combination blueberries.

21. The method for treating oxidative stress (OS) as claimed in claim 1 including in the combination cranberries.

22. The method for treating oxidative stress (OS) as claimed in claim 1 including in the combination blueberries and cranberries.

\* \* \* \* \*